United States Patent [19]
Baker et al.

[11] Patent Number: 5,863,947
[45] Date of Patent: Jan. 26, 1999

[54] PHENYLGLYCINE DERIVATIVES USEFUL FOR TREATING DISORDERS OF THE CENTRAL NERVOUS SYSTEM

[75] Inventors: Stephen Richard Baker, Yateley; Barry Peter Clark, Lower Froyle; John Goldsworthy, Basingstoke; John Richard Harris, Guildford, all of United Kingdom

[73] Assignee: Eli Lilly and Company Limited, Basingstoke, England

[21] Appl. No.: 853,285

[22] Filed: May 9, 1997

[30] Foreign Application Priority Data

May 13, 1996 [GB] United Kingdom .................. 9609976

[51] Int. Cl.$^6$ .................. A61K 31/195; A61K 31/34; A61K 31/38; A61K 31/40; C07C 229/36; C07C 321/28; C07D 295/155; C07D 307/54; C07D 333/24

[52] U.S. Cl. .................. 514/567; 514/429; 514/438; 514/471; 514/562; 514/564; 548/577; 549/77; 549/496; 562/432; 562/437; 562/441; 562/443; 562/444; 562/449

[58] Field of Search .................. 514/429, 438, 514/471, 562, 564, 567; 549/77, 496; 548/577; 562/432, 437, 441, 443, 444, 449

[56] References Cited

U.S. PATENT DOCUMENTS 5,238,958  8/1993  Johnson et al. .
5,610,183  3/1997  Owens et al. .................. 514/567 X

FOREIGN PATENT DOCUMENTS

WO 95/15941  6/1995  WIPO .

OTHER PUBLICATIONS

"Structure–activity relationships of new agonists and antagonists of different motabotropic glutamate receptor subtypes", British Journal of Pharmacology (1996), vol. 117, pp. 1493–1503.

Chemical Abstarcts 110:6394 (1988).
Chemical Abstracts 107:176434 (1987).
Cas Registry No. 116435–35–9.
Harris, C.M. et al. Tetrahedron Letters,(8), 705–708 (1978).
Harris, C.M. et al. Journal of the American Chemical Society, 101(2), 437–445 (1979).

Primary Examiner—Michael G. Ambrose
Attorney, Agent, or Firm—Martin A. Hay; David E. Boone

[57] ABSTRACT

A pharmaceutical compound of the formula:

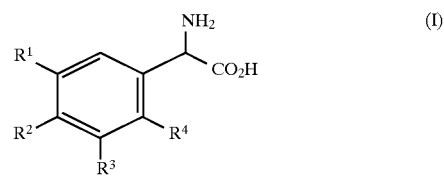

in which $R^1$ is hydrogen, hydroxy or $C_{1-6}$ alkoxy, $R^2$ is hydrogen, carboxy, tetrazolyl, —SO$_2$H, —SO$_3$H, —OSO$_3$H, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or aryl $C_{1-6}$ alkyl, $R^3$ is hydrogen, hydroxy or $C_{1-4}$ alkoxy, and $R^4$ is fluoro, trifluoromethyl, nitro, $C_{1-6}$ alkyl, $C_{3-7}$ cycloalkyl, $C_{2-6}$ alkenyl, $C_{2-6}$ alkynyl, $C_{1-6}$ alkylthio, heteroaryl, optionally substituted aryl, optionally substituted aryl $C_{1-6}$ alkyl, optionally substituted aryl $C_{2-6}$ alkenyl, optionally substituted aryl $C_{2-6}$ alkynyl, optionally substituted aryloxy, optionally substituted aryl $C_{1-6}$ alkoxy, optionally substituted arylthio, optionally substituted aryl $C_{1-6}$ alkylthio or —CONR"R'", —SO$_2$NR"R'", —NR"R'", —OCONR"R'" or —SONR"R'" where R" and R'" are each hydrogen, $C_{1-6}$ alkyl or aryl $C_{1-6}$ alkyl, or R" and R'" together form a $C_{3-7}$ alkylene ring;

provided that (i) $R^1$, $R^2$ and $R^3$ are not all hydrogen, and (ii) when $R^2$ and $R^3$ are hydrogen and $R^1$ is hydroxy, $R^4$ is not fluoro;

or a salt or ester thereof.

12 Claims, No Drawings

PHENYLGLYCINE DERIVATIVES USEFUL FOR TREATING DISORDERS OF THE CENTRAL NERVOUS SYSTEM

This invention relates to novel compounds and their use as pharmaceuticals.

Certain phenyl glycine compounds are disclosed in WO 95/15941 as having CNS influencing properties. In general these compounds lack a substituent at the 2-position of the phenyl ring. Compounds of a similar structure are also disclosed in Br. J. Pharmacol. (1996) 117, 1493.

The compounds of the invention are of the formula:

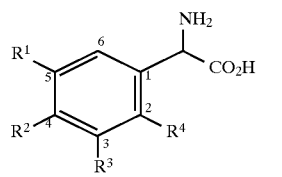

in which $R^1$ is hydrogen, hydroxy or $C_{1-6}$ alkoxy, $R^2$ is hydrogen, carboxy, tetrazolyl, —$SO_2H$, —$SO_3H$, —$OSO_3H$, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or aryl $C_{1-6}$ alkyl, $R^3$ is hydrogen, hydroxy or $C_{1-4}$ alkoxy, and $R^4$ is fluoro, trifluoromethyl, nitro, $C_{1-6}$ alkyl, $C_{3-7}$ cycloalkyl, $C_{2-6}$ alkenyl, $C_{2-6}$ alkynyl, $C_{1-6}$ alkylthio, heteroaryl, optionally substituted aryl, optionally substituted aryl $C_{1-6}$ alkyl, optionally substituted aryl $C_{2-6}$ alkenyl, optionally substituted aryl $C_{2-6}$ alkynyl, optionally substituted aryloxy, optionally substituted aryl $C_{1-6}$ alkoxy, optionally substituted arylthio, optionally substituted aryl $C_{1-6}$ alkylthio or —CONR"R'", —$SO_2NR"R'"$, —NR"R'", —OCONR"R'" or —SONR"R'" where R" and R'" are each hydrogen, $C_{1-6}$ alkyl or aryl $C_{1-6}$ alkyl, or R" and R'" together form a $C_{3-7}$ alkylene ring;

provided that (i) $R^1$, $R^2$ and $R^3$ are not all hydrogen, and (ii) when $R^2$ and $R^3$ are hydrogen and $R^1$ is hydroxy, $R^4$ is not fluoro;

or a salt or ester thereof.

The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above general formula, a $C_{1-6}$ alkyl group can be straight or branched chain, such as, for example, methyl, ethyl, propyl, isopropyl, butyl and isobutyl, and is preferably methyl or ethyl. A $C_{1-6}$ alkoxy or a $C_{1-6}$ alkylthio is one such alkyl group linked through an oxygen or sulfur atom respectively. A $C_{2-6}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula R—CH=CH— where R is $C_{1-4}$ alkyl. A $C_{2-6}$ alkynyl group includes, for example, prop-2-ynyl, but-3-ynyl, and pent-4-ynyl. An alkynyl group can contain more than one triple bond and can contain, in addition, one or more double bond. A preferred alkynyl group is of the formula:

R—C≡C— where R is $C_{1-4}$ alkyl. A $C_{3-7}$ cycloalkyl group is preferably, for example, cyclopropyl, cyclopentyl or cyclohexyl and these groups may optionally be substituted by one or two methyl substituents.

In the above Formula (I), an aryl group is preferably phenyl or naphthyl, and an optionally substituted phenyl or naphthyl group is optionally substituted with, for example, one or more substituents, preferably 1 to 3 substituents, selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino, $C_{1-4}$ acylamino and $C_{1-4}$ alkylthio. A naphthyl group can be 1-naphthyl or 2-naphthyl. When substituted, a phenyl or naphthyl group is preferably substituted by one to three substituents. An aryl $C_{1-6}$ alkyl group is one such group linked through an alkylene chain, for example, aryl $(CH_2)_n$ where n is 1 to 6, and a most preferred example is benzyl. Preferred examples of groups are as follows:

aryloxy—optionally subsituted phenoxy;

aryl $C_{1-6}$ alkoxy—optionally substituted phenylmethoxy or phenylethoxy;

arylthio—optionally substituted phenylthio;

aryl $C_{1-6}$ alkylthio—optionally subsituted phenylmethylthio or phenylethylthio.

A heteroaryl group can be any aryl group having one or more hetero atoms in the ring. The term includes fused ring structures. Preferably the heteroaryl group contains one or two hetero atoms selected from oxygen, nitrogen and sulphur. It preferably contains from 5 to 10 carbon atoms, and for example may be of the formula:

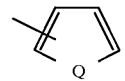

where Q is —O—, —S— or —NR—, and R is hydrogen or $C_{1-4}$ alkyl. Alternatively, a heteroaryl group comprises a benzene fused ring as, for example:

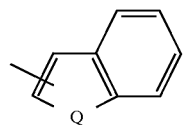

and further heteroaryl groups include:

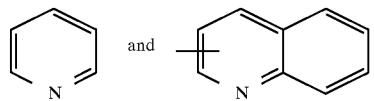

Especially preferred heteroaryl groups are pyrrolyl, thienyl or furanyl, preferred examples being 2-thienyl and 2-furanyl, and also pyridyl, in particular 2- and 3-pyridyl.

The group $R^2$ is preferably hydrogen, carboxy or tetrazolyl and especially carboxy, and the group $R^4$ is preferably $C_{1-6}$ alkyl, $C_{2-6}$ alkenyl, optionally substituted phenyl, optionally substituted phenyl $C_{1-6}$ alkyl, optionally substituted phenoxy, optionally substituted phenylthio or optionally substituted phenyl $C_{1-6}$ alkylthio.

The groups $R^1$ and $R^3$ are each preferably hydrogen or hydroxy.

A preferred group of compounds of formula (I) above, is one in which $R^1$ is hydrogen, $R^2$ is carboxy, $R^3$ is hydrogen or hydroxy and $R^4$ is $C_{1-6}$ alkyl, especially methyl or ethyl.

A further preferred group of compounds of formula (I) above is one in which $R^1$ is hydrogen or hydroxy, $R^2$ is hydrogen or carboxy, $R^3$ is hydrogen or hydroxyl and $R^4$ is $C_{1-6}$ alkyl, $C_{2-6}$ alkenyl, optionally substituted phenyl, optionally substituted phenyl $C_{1-6}$ alkyl, optionally substituted phenoxy, optionally substituted phenylthio or optionally substituted phenyl $C_{1-6}$ alkylthio.

A further preferred group of compounds of formula (I) is one in which $R^1$ is hydrogen, $R^2$ is carboxy, $R^3$ is hydrogen and $R^4$ is as defined above.

A further preferred group of compounds of formula (I) is one in which $R^1$ is hydroxyl, $R^2$ is hydrogen, $R^3$ is hydroxyl and $R^4$ is as defined above, and is especially $C_{1-6}$ alkyl or optionally substituted phenyl $C_{1-6}$ alkyl, for example benzyl.

A further preferred group of compounds of formula (I) is one in which $R^1$ is hydrogen, $R^2$ is carboxy, $R^3$ is hydroxyl and $R^4$ is as defined above, and is especially $C_{1-6}$ alkyl or optionally substituted phenyl $C_{1-6}$ alkyl, for example benzyl.

Two particularly preferred compounds are:

(1) 2-(4-carboxy-2-methylphenyl)glycine, especially the (+)- enantiomer, and (2) 2-amino-2-(2-methyl-3-hydroxy-4-carboxyphenyl) acetic acid.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention contain one or more asymmetric carbon atoms, and this gives rise to enantiomers. In general the S-isomers at the α carbon atom are preferred. The compounds can be prepared as racemates or as enantiomers, and individual enantiomers can be isolated from racemates by conventional techniques if so desired.

The invention also includes a process for producing the compounds of the invention, which comprises:

1) hydrolysing a compound of the formula:

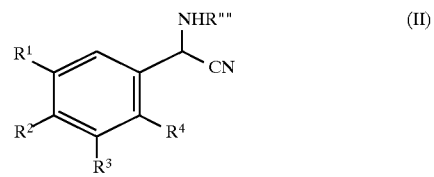

where R"" is an acyl group such as, for example, acetyl or 2) hydrolysing a compound of the formula:

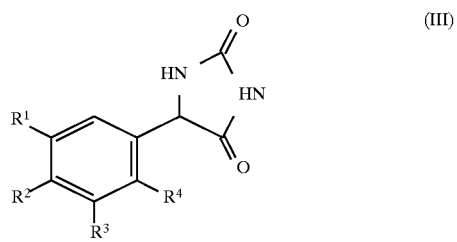

With regard to process variant (1), this reaction is preferably carried out in a solvent such as, for example, water, at an elevated temperature of from 80° C. to 150° C., and with the aid of an acid or base such as, for example, hydrochloric acid or sodium hydroxide.

Compounds of formula (II) can be prepared from the corresponding aldehyde, of formula:

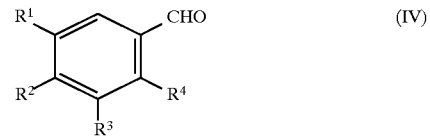

by reacting with nitrile as, for example, potassium cyanide, and ammonium halide, under the conditions of the Strecker reaction followed by acylation with, for example, acetyl chloride and di-isopropylethylamine. Compounds of formula (IV) are either known or can be made by methods that are known in the art, and may be protected prior to reaction with substituent protected groups $R^{1'}$, $R^{2'}$, $R^{3'}$ and $R^{4'}$, said protected groups being converted to the desired substituent at a later stage.

With regard to process variant (2), this reaction is preferably carried out in a solvent such as, for example, water, at an elevated temperature of from 50° C. to 150° C., and in the presence of an acid or base such as, for example, hydrochloric acid or sodium hydroxide.

Compounds of formula (III) can be prepared by reacting compounds of formula (IV) with potassium cyanide and ammonium carbonate in aqueous ethanol under the conditions of the Bucherer Bergs reaction.

The compounds described above have pharmaceutical activity. They have been shown to possess affinity for metabotropic glutamate receptors.

Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-aspartate, AMPA, and kainate (Sommer B. and Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. and Conn J. P., Trends Pharmacol. Sci. 14: 13–20, 1993). Metabotropic glutamate receptors can be selectively activated by 1S,3R-1-aminocyclopentane-1,3-dicarboxylic acid (1S,3R-ACPD).

The compounds of the invention block the metabotropic glutamate receptor second messenger responses with IC50 values of less than 100 µM, including stimulation of phosphoinositide hydrolysis by agonist (Schoepp D. D., Johnson B. G., True R. A., and Monn J. A., Eur. J. Pharmacol.—Mol. Pharmacol. Section 207: 351–353, 1991) and reversal of 1S,3R-ACPD-induced inhibition of forskolin-stimulated cAMP formation (Schoepp D. D., Johnson B. G., and Monn J. A., J. Neurochem. 58: 1184–1186, 1992).

The affinity of the compounds for metabotropic glutamate receptors has also been demonstrated by the selective displacement of 1S,3R-ACPD-sensitive $^3$H-glutamate binding to rat brain cell membranes, a test for metabotropic glutamate receptor activity described by Schoepp D. D. and True R. A. (Neuroscience Lett. 145: 100–104, 1992). The preferred compounds of the invention have an IC50 value of less than 100 µM.

The compounds of the invention are thus indicated for use in the treatment of neurological disorders such as acute neurodegenerative diseases, for example stroke, cerebral ischemia and head and spinal cord trauma, and chronic neurodegenerative diseases such as for example Alzheimer's disease, Parkinson's disease, Amyotrophic lateral sclerosis, AIDS-induced dementia and Huntington's Chorea. The compounds are also indicated for use as antipsychotic, anticonvulsant, anti-emetic and analgesic agents. They are thus of potential use in the treatment of pain, and also have potential as anxiolytic and antidepressant agents.

The invention also includes a pharmaceutical composition comprising a pharmaceutically-acceptable diluent or carrier in association with a compound of Formula (I), or a pharmaceutically-acceptable salt thereof.

The compounds may be administered by various routes, for example, by the oral or rectal route, topically or parentally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

EXAMPLE 1

2-(4-Carboxy-2-methylphenyl)glycine i) To a stirred solution of 4-bromo-3-methylbenzonitrile (4 g, 20 mmol) in tetrahydrofuran (100 ml), cooled to –100° C. under a nitrogen atmosphere, was added dropwise a solution of n-butyllithium in hexanes (1.6M, 12.8 ml). After addition, the pale red solution was stirred for 5 minutes at –100° C. and dry dimethylformamide (2.2 ml) then added dropwise. After 20 minutes, during which the temperature reached –60° C., the reaction mixture was poured onto a saturated solution of sodium chloride (100 ml). The organic phase was separated and combined with a diethyl ether (100 ml) wash of the aqueous phase, dried, filtered and evaporated. Crystallised from diethyl ether-hexane to give 4-cyano-2-methylbenzaldehyde as a white solid.

ii) A stirred mixture of 4-cyano-2-methylbenzaldehyde (8 g, 55 mmol), potassium cyanide (6.46 g, 99 mmol) and ammonium carbonate (19.08 g, 199 mmol) in ethanol-water (1:1, 30 ml) was heated to 85° C. for 3 hours in a PTFE lined stainless steel sealed reaction vessel. The cooled mixture was diluted with water and cautiously acidified with concentrated hydrochloric acid. After decanting, the solution was saturated with sodium chloride and extracted with ethyl acetate (4×) to give a red oil. Attempted crystallisation from ethyl acetate gave an off-white solid contaminated with ammonium salts. The filtrate was evaporated and recrystallised from isopropyl alcohol to give 5-(4-cyano-2-methylphenyl)hydantoin as a pale brown solid. The filtrate was evaporated and chromatography on flash silica eluting with ethyl acetate-dichloromethane (4:1) gave more 5-(4-cyano-2-methylphenyl)hydantoin as a foam.

iii) A stirred mixture of 5-(4-cyano-2-methylphenyl) hydantoin (1.1 g, 5.2 mmol) in aqueous sodium hydroxide (2M, 12 ml) was heated to 120° C. for 17 hours in a PTFE lined stainless steel sealed reaction vessel. The cooled mixture was acidified with glacial acetic acid (1.4 ml) and chromatographed on ion exchange (Dowex 50×8–100 resin). The column was eluted sequentially with water, tetrahydrofuran-water (1:1), water and 10% pyridine in water. Fractions collected from the pyridine-water elution were combined and evaporated to dryness, redissolved in water and freeze-dried to give the title compound as a white powder, m.p. >250° C.

EXAMPLE 2

(S)-2-(4-Carboxy-2-methylphenyl)glycine

Racemic 2-(4-carboxy-2-methylphenyl)glycine (9.2 g, 44 mmol) and D-lysine (6.43 g, 44 mmol) were dissolved in warm water (60 ml). The solution was filtered to remove trace insolubles and then diluted with methanol (200 ml) and diethyl ether (20 ml). An initial precipitate was removed by filtration and the filtrate allowed to stand. After 6 hours the supernatant was decanted from solid and the solid washed with methanol. The solid was then re-crystallised twice from water-methanol and the resulting crystals washed with water-methanol (1:1), methanol and diethyl ether. The white crystals were dried in vacuo, dissolved in water and chromatographed on ion exchange (Dowex 50×8–100 resin). The column was eluted with water, and 10% pyridine in water, fractions collected from the pyridine-water elution were combined and evaporated to dryness. The product was partially dissolved in water and freeze-dried $[\alpha]D^{26}$ at 147° C. (C=0.26) in aqueous hydrochloric acid (5M).

EXAMPLE 3

2-(4-Carboxy-2-fluorophenyl)glycine i) A stirred mixture of 4-bromo-2-fluorobenzaldehyde (39 g, 192 mmol) and cuprous cyanide (18.9 g, 211 mmol) in dimethylformamide (100 ml) was heated to 150° C. for 12 hours under nitrogen atmosphere. The dark solution was cooled and a solution of ferric chloride (34 g, 211 mmol) in hydrochloric acid (2M, 100 ml) was added, followed by water (100 ml). Solid crystallised from the mixture and was filtered, washed with water and dried at 40° C. in vacuo. Recrystallisation from cyclohexane (500 ml) gave 4-cyano-2-fluorobenzaldehyde (m.p. 79° C.) as yellow needles.

ii) A stirred mixture of 4-cyano-2-fluorobenzaldehyde (1.94 g, 13 mmol), potassium cyanide (1.69 g, 26 mmol) and ammonium carbonate (4.99 g, 52 mmol) in ethanol-water ((1:1, 20 ml) was heated to 80° C. for 12 hours in a PTFE lined stainless steel sealed reaction vessel. The cooled mixture was diluted with water and cautiously acidified with concentrated hydrochloric acid (15 ml). Extraction with chloroform (2×30 ml) gave 5-(4-cyano-2-fluorophenyl)hydantoin as a yellow glass.

iii) A stirred mixture of 5-(4-cyano-2-fluorophenyl)hydantoin (0.4 g, 1.8 mmol) in sodium hydroxide (2M, 4 ml, 8 mmol) was heated under reflux for 20 hours. The solution was cooled, acidified to pH~4 with 5M hydrochloric acid (1 ml) and chromatographed on ion exchange (Dowex 50×8–100 resin). The column was eluted sequentially with water, tetrahydrofuran-water (1:1), water, 10% pyridine in water. Fractions collected after the pyridine-water elution were combined, evaporated to dryness, redissolved in water and freeze-dried to give the title product as an off-white powder, m.p. 250°–5° C.

EXAMPLE 4

2-Amino-2-(4-carboxy-2-phenylthiophenyl)acetic acid i) A stirred mixture of 4-cyano-2-fluorobenzaldehyde (1.49 g, 10 mmol), thiophenol (1.21 g, 11 mmol) and potassium carbonate (1.21 g, 11 mmol) in dimethylformamide (10 ml) was heated to 90° C. for 30 minutes under nitrogen atmosphere. The mixture was cooled, diluted with water (10 ml) and the precipitate filtered, washed with water and dried (2.45 g). Recrystallisation from isopropylalcohol (20 ml) gave 4-cyano-2-phenylthiobenzaldehyde as yellow needles, m.p. 88° C.

ii) A stirred mixture of 4-cyano-2-phenylthiobenzaldehyde (1.43 g, 6 mmol), potassium cyanide (0.78 g, 12 mmol) and ammonium carbonate (2.30 g, 24 mmol) in ethanol-water (1:1, 20 ml) was heated to 85° C. for 4 hours in a sealed pressure vessel. The mixture was cooled, diluted with water (20 ml) and cautiously acidified with hydrochloric acid (5M, 12 ml). The mixture was extracted with diethyl ether (2×20 ml) and the extracts dried, filtered and evaporated to a brown oil. Chromatography on flash silica eluting with 5% methanol in chloroform gave 5-(4-cyano-2-phenylthiophenyl)hydantoin as a yellow solid.

iii) A stirred solution of 5-(4-cyano-2-phenylthiophenyl)hydantoin (0.5 g, 1.62 mmol) in 2M sodium hydroxide (4 ml, 8 mmol) was heated under reflux for 24 hours under nitrogen atmosphere. The cooled solution was acidified with 5M hydrochloric acid (2 ml) to pH~4 and the precipitated solid filtered and washed with diethyl ether. The solid was dissolved in water (10 ml) and ammonia solution (0.88 g, 0.4 ml), filtered and the filtrate acidified with acetic acid (0.5 ml) to pH~4. The title product crystallised on standing as off-white crystals, m.p. 266°–271° C.

EXAMPLE 5

2-Amino-2-(4-carboxy-2-[(2-phenylethyl)thio]phenyl)acetic acid i) Phenylethylmercaptan (2.14 ml, 16 mmol) was added to a stirred suspension of 4-cyano-2-fluorobenzaldehyde (2.23 g, 15 mmol) and potassium carbonate (2.21 g, 16 mmol) in dimethylformamide (10 ml) at room temperature under nitrogen atmosphere. The mixture was heated to 75° C. for 1 hour, then cooled and diluted with water (15 ml). A yellow solid precipitated and was filtered, washed with water and then crystallised from cyclohexane (250 ml) to give pale needles of 4-cyano-2-(2-phenylethylthio)benzaldehyde, m.p. 89° C.

ii) A stirred mixture of 4-cyano-2-(2-phenylethylthio)benzaldehyde (2.14 g, 8 mmol) potassium cyanide (1.04 g, 16 mmol) and ammonium carbonate (3.07 g, 32 mmol) in ethanol-water (1:1, 20 ml) was heated to 80° C. for 2 hours in a sealed pressure vessel. The cooled solution was diluted with water (30 ml) to precipitate a sticky solid, filtered, washed with water and triturated with CHCl₃ (20 ml) to give 5-(4-cyano-2-(2-phenylethylthio)phenyl)hydantoin, m.p. 198° C.

iii) A stirred solution of 5-(4-cyano-2-(2-phenylethylthio)phenyl)hydantoin (1.20 g, 3.56 mmol) in 2M sodium hydroxide (10 ml, 20 mmol) was heated under reflux for 72 hours. The cooled solution was acidified with 5M hydrochloric acid (2 ml, 20 mmol), then with acetic acid (1 ml) to pH~4. The pale solid was filtered (0.9 g), washed with CHCl₃ (10 ml) and redissolved in water (10 ml) and 0.880 ammonia solution (0.1 ml). The solution was acidified with acetic acid (0.4 ml) to precipitate a fine solid that was filtered and washed with methanol to give the title product as an off-white solid, m.p. 227°–231° C.

EXAMPLE 6

2-Amino-2(2-benzylthio-4-carboxyphenyl)acetic acid i) A mixture of 4-cyano-2-fluorobenzaldehyde (1.49 g, 10 mmol), phenyl mercaptan (1.39 g, 11 mmol), potassium carbonate (1.51 g, 11 mmol) in dimethylformamide (20 ml) was heated with stirring under a nitrogen atmosphere for 1 hour 40 minutes at 90° C. The yellow solution was cooled, then diluted with water (40–50 ml). The resulting precipitate was filtered and washed with more water, then dried. Recrystallisation from isopropanol gave 2-benzylthio-4-cyanobenzaldehyde as a yellow solid, m.p. 106°–109° C.

ii) A mixture of 2-benzylthio-4-cyanobenzaldehyde (1.38 g, 5 mmol), potassium cyanide (0.78 g, 12 mmol) and ammonium carbonate (2.304 g, 24 mmol) in ethanol-water (1:1, 16 ml) was heated with stirring in a sealed reaction vessel at 85° C. for 16 hours. The resulting cooled solution was acidified with 2N hydrochloric acid (6 ml), then extracted with ethyl acetate (3×10 ml), dried and evaporated to a pale brown solid. Chromatography on flash silica eluting with ether/hexane 4:1 gave 5-(2-benzylthio-4-cyanophenyl)hydantoin as a pale orange solid.

iii) A solution of 5-(2-benzylthio-4-carboxyphenyl) hydantoin (0.375 g, 0.12 mmol) in 2N sodium hydroxide (6 ml, 12 mmol) was heated with stirring in a sealed reaction vessel for 20 hours at 120° C. The cooled solution was acidified wih 2N hydrochloric acid (1 ml) to pH~4 and chromatographed on ion exchange (Dowex 50×8–100). The column was eluted sequentially with water, tetrahydrofuran-water (1:1), water, then 10% pyridine in water. Fractions collected after pyridine water were combined, evaporated to dryness, redissolved in water, then freeze-dried to give the title product as an off-white solid, m.p. ~226° C.

EXAMPLE 7

4-Carboxy-2-phenoxyphenylglycine i) A stirred mixture of 4-cyano-2-fluorobenzaldehyde (2.23 g, 15 mmol), phenol (1.6 g, 17 mmol) and potassium carbonate (2.35 g, 17 mmol) in dried dimethylformamide (15 ml) was heated to 120° C. for 1 hour. After cooling, the mixture was diluted with water (50 ml) and extracted with diethyl ether (2×25 ml). The extracts were washed with 0.1M sodium hydroxide (2×50 ml), brine (50 ml), dried, filtered and evaporated to a yellow oil. Flash chromatography on silica, eluting with diethyl ether:hexane 1:1, gave 4-cyano-2-phenoxybenzaldehyde as a yellow oil that crystallised on standing.

ii) A stirred mixture of 4-cyano-2-phenoxybenzaldeyde (2.23 g, 10 mmol), potassium cyanide (1.30 g, 20 mmol) and ammonium carbonate (3.84 g, 40 mmol) in ethanol-water (30 ml, 1:1) was heated to 80° C. for 2 hours in a sealed vessel. The mixture was diluted with water (30 ml), cautiously acidified to pH1 with 5M hydrochloric acid (20 ml) and extracted with ethyl acetate (30 ml). The extracts were washed with water (30 ml), dried, filtered and evaporated to a viscous brown oil (3.1 g). Chromatography on flash silica (graded elution with 2 to 4% methanol in dichloromethane) gave 5-(4-cyano-2-phenoxyphenyl)hydantoin as a yellow foam.

iii) A stirred solution of 5-(4-cyano-2-phenoxyphenyl)hydantoin (1.10 g, 3.75 mmol) in 2M sodium hydroxide (20 ml) was heated under reflux for 48 hours. The cooled solution was party neutralised with 5M hydrochloric acid (4 ml) and chromatographed directly on ion exchange (Dowex 50×8–100 resin). Sequential elution with water, tetrahydrofuran-water (1:1), water and finally 10% pyridine in water gave the title product as a white solid after freezedrying, m.p. 258°–266° C.

EXAMPLE 8

2-(4-Carboxy-2-methoxyphenyl)glycine i) To a stirred solution of 4-cyano-2-fluorobenzaldehyde (0.5 g, 3.4 mmol) in dry dimethylformamide (3 ml) cooled to 5° C. under a nitrogen atmosphere, a solution of freshly prepared sodium methoxide in methanol (1.41M, 2.62 ml) was added slowly, dropwise. After addition, the reaction mixture was stirred at room temperature for 22 hours. A few drops of water were then added and the turbid solution filtered through celite. The filtrate was further diluted with water until crystallisation commenced to give 2-cyano-4-methoxybenzaldeyde as a pale yellow solid. A second crop was recovered from the filtrate.

ii) 4-Cyano-2-methoxybenzaldehyde (0.86 g, 5.34 mmol) was reacted with potassium cyanide (0.7 g, 10.64 mmol) and ammonium carbonate (2.05 g, 21.36 mmol) following the procedure described in Example 1 (ii). The crude solid obtained after extraction was chromatographed on flash silica eluting with ethylacetate-hexane (4:1) to give 5-(4-cyano-2-methoxyphenyl)hydantoin as a pale yellow solid.

iii) 5-(4-Cyano-2-methoxyphenyl)hydantoin (0.29 g, 1.26 mmol) was hydrolysed with aqueous sodium hydroxide (2M, 6 ml) at 85° C. and worked up following the procedure described in Example 1 (iii) to give the title compound as a white solid.

EXAMPLE 9

2-Amino-2-[4-carboxy-2-(1-pyrrolidinyl)phenyl]acetic acid i) Pyrrolidine (1.67 ml, 20 mmol) was added to a stirred mixture of 4-cyano-2-fluorobenzaldehyde (2.23 g, 15 mmol) and potassium carbonate (2.21 g, 16 mmol) in dry dimethylformamide. The mixture was heated to 90° C. for 8 hours under reflux, extra pyrrolidine (1.67 ml) added and heated for a further 8 hours. The mixture was diluted with water (20 ml), extracted with diethyl ether (2×30 ml) and the extracts dried, filtered, and evaporated to a brown oil. The oil was chromatographed on flash silica, eluting with chloroform, to give a yellow solid (1.25 g). Recrystallisation from cyclohexane (50 ml) gave yellow needles of 4-cyano-2-(1-pyrrolidinyl)benzaldehyde, m.p. 121° C.

ii) A stirred mixture of 4-cyano-2-(1-pyrrolidinyl) benzaldehyde (0.50 g, 2.5 mmol), potassium cyanide (0.32 g, 5 mmol) and ammonium carbonate (0.96 g, 10 mmol) in 1:1 ethanol-water (10 ml) was heated to 75° C. for 2 hours in a sealed vessel. After dilution with water (20 ml), a solid precipitated on standing. The solid was filtered, washed with water, and then triturated with chloroform to give 5-(4-cyano-2-(1-pyrrolidinyl)phenyl) hydantoin as a yellow solid, m.p. 154° C.

iii) A stirred solution of 5-(4-cyano-2-(1-pyrrolidinyl) phenyl)hydantoin (95 mg, 0.35 mmol) in 2M sodium hydroxide (2 ml, 4 mmol) was heated under reflux for 24 hours. The solution was partly neutralised with 2M hydrochloric acid (1 ml) and then chromatographed on ion exchange resin as described in Example 3(iii) to give the title product as an off-white solid, m.p. 187°–190° C.

EXAMPLE 10

2-Amino-2-[2-(N-benzyl-N-methylamino)-4-carboxy-phenyl]acetic acid i) A stirred mixture of 4-cyano-2-fluorobenzaldehyde (2.83 g, 19 mmol), N-benzyl-N-methylamine (5.2 ml, 40 mmol) and potassium carbonate (5.56 g, 40 mmol) in dimethylformamide (20 ml) was heated with stirring under a nitrogen atmosphere to 90° C. for 1.5 hours. After allowing the reaction mixture to cool, water was added (30 ml). A yellow solution with an oily precipitate formed. This was extracted with ethyl acetate (4×10 ml), combined, dried, then evaporated to yield a brown oil.

Chromatography on flash silica eluting with ether/hexane (1:1) gave 4-cyano-2-(N-benzyl-N-methylamino) benzaldehyde as a brown/orange oil.

ii) A stirred mixture of 4-cyano-2-(N-benzyl-N-methylamino)benzaldeyde (3.55 g, 14 mmol), potassium cyanide (1.85 g, 28.4 mmol) and ammonium carbonate (5.45 g, 56.8 mmol) in ethanol-water (15 ml, 1:1) was heated at 85° C. for 24 hours following the procedure described in Example 1 (ii). The crude brown solution/oil was acidified with 5N hydrochloric acid (12 ml) to form a brown solution with some gluey solids. An ethyl acetate extraction (3×30 ml) was carried out with the combined organics, and the product dried and evaporated to yield a pale brown/orange solid.

Chromatography on flash silica eluting with ethyl acetate/hexane (4:1) gave 5-(4-cyano-2-(N-benzyl-N-methylamino) phenyl)hydantoin as an orange solid, m.p. 95°–98° C.

iii) A stirred mixture of 5-(4-cyano-2-(N-benzyl-N-methylamino)phenyl)hydantoin (1.55 g, 4.8 mmol) in 2M sodium hydroxide (24 ml, 48 mmol) in a sealed vessel was heated to 120° C. for 2 days. It was worked up as Example 4 (iii) to give the title compound as an off-white fluffy solid. Further purification by high pressure liquid chromatography (column 250×4.6 mm id. KR100-S C18) eluting with water/acetonitrile/ammonia (25%/75%/0.1%) gave the title compound as a white fluffy solid, m.p. 193° C.

EXAMPLE 11

2-Amino-2-(4-carboxy-2-phenylphenyl)acetic acid i) A mixture of 4-cyano-2-fluorobenzaldehyde (11.73 g, 78.7 mmol) and potassium carbonate (14.12 g, 102.3 mmol) was dissolved in dry dimethylformamide (35 ml). To this was added water (6.63 ml, 368.5 mmol). The resulting solution was heated to 90° C. with stirring. A further equivalent of water (1.42 ml) was added after 2 hours, then a further two equivalents of water (2.84 ml) 1 hour later. The resulting solution was left overnight. After 24 hours a further 2 equivalents of water (2.84 ml) was added, then heated for a further 2 hours at 90° C. The cooled solution was diluted with water to form a murky yellow solution. The solid precipitate was filtered. The remaining yellow filtrate was acidified with concentrated hydrochloric acid to produce a yellow solid. This was filtered, then dried at 40° C. overnight to give 4-cyano-2-hydroxybenzaldehyde as a yellow solid.

ii) A stirred solution of 4-cyano-2-hydroxybenzaldehyde (10.15 g, 69 mmol), 4-dimethylaminopyridine (1.69 g, 14 mmol) and 2,6-lutidine (9.3 g, 86 mmol) in dichloromethane (120 ml) was cooled under an atmosphere of nitrogen to −70° C. and trifluoromethylsulphonic anhydride (24.4 g, 86 mmol) added dropwise over a period of 2 minutes. The resulting mixture was allowed to warm to −40° C. and after 1.5 hours washed with water (100 ml), aqueous hydrochloric acid (0.5M, 100 ml), water (2×100 ml) and a saturated solution of sodium chloride. The organic phase was dried, filtered and evaporated to a solid. The solid was suspended in dichloromethane and purified by short path chromatography on flash silica, eluting with dichloromethane-hexane (1:1) to give 4-cyano-2-trifluoromethylsulphonylbenzaldehyde as a yellow oil which solidified on standing.

iii) Tetrakis(triphenylphosphine)palladium [0] (40 mg) was added to a stirred mixture of 4-cyano-2-trifluoromethylsulphonylbenzaldehyde (0.45 g, 1.6 mmol), lithium chloride (0.2 g, 4.8 mmol) and tri-n-butylphenylstannane (0.55 ml, 1.7 mmol) in dried dioxan (10 ml) under nitrogen atmosphere. The resulting suspension was heated under reflux for 24 hours. The dark mixture was cooled, and aqueous potassium fluoride solution (30 ml) and ethyl acetate (30 ml) were added. After vigorous stirring, the black precipitate was filtered and the filtrate layers separated. The ethyl acetate solution was washed with brine (30 ml), dried, filtered and evaporated to a yellow semi-solid (0.72 g). Chromatography on flash silica eluting with chloroform gave 4-cyano-2-phenylbenzaldehyde as a white solid, m.p. 75° C.

iv) A stirred mixture of 4-cyano-2-phenylbenzaldehyde (0.15 g, 0.7 mmol), ammonium carbonate (0.27 g, 2.8 mmol) and potassium cyanide (91 mg, 1.4 mmol) in ethanol-water (1:1, 4 ml) was heated to 85° C. for 4 hours in a sealed vessel. After cooling, the mixture was diluted with water (2 ml) and cautiously acidified to pH1 precipitating a sticky solid. The crude solid was dissolved in 2M sodium hydroxide and heated to 120° C. for 16 hours in a sealed vessel. After cooling, the reaction solution was chromatographed directly on ion exchange resin, as described in Example 3 (iii) to give the title product as a white solid, m.p. 238°–240° C.

EXAMPLE 12

2-Amino-2[4-carboxy-2-(2-thienyl)phenyl]acetic acid i) 4-Cyano-2-trifluoromethylsulphonylbenzaldehyde was reacted with 2-(2-tributylstannyl)thiophene using the method described in Example 11 (iii) and the product recrystallised from isopropyl alcohol to give tan coloured needles of 4-cyano-2-(2-thienyl)benzaldehyde, m.p. 114° C.

ii) A stirred mixture of 4-cyano-2-(2-thienyl)benzaldehyde (0.50 g, 2.3 mmol), ammonium carbonate (0.90 g, 9.4 mmol) and potassium cyanide (0.30 g, 4.7 mmol) in ethanol-water (1:1, 10 ml) was heated to 85° C. for 16 hours in a sealed vessel. After cooling, the mixture was diluted with water and cautiously acidified to precipitate a brown lumpy solid on standing. The product was filtered and triturated with dichloromethane (10 ml) to give 4-cyano-2-(2-thienyl)phenyl hydantoin as a brown solid, m.p. 189° C.

iii) 4-Cyano-2-(2-thienyl)phenyl hydantoin was hydrolysed using the method described in Example 1 (iii) to give the title product as a pale yellow solid, m.p. 185°–188° C. dec.

EXAMPLE 13

2-Amino-2[4-carboxy-2(2-furanyl)phenyl]acetic acid i) 4-Cyano-2-trifluoromethylsulphonylbenzaldehyde was reacted with 2-(2-tributylstannyl)furan using the method described in Example 11(iii) and the product recrystallised from isopropyl alcohol to give yellow needles of 4-cyano-2(2-furanyl)benzaldehyde, m.p. 125° C.

ii) 4-Cyano-2(2-furanyl)benzaldehyde was reacted as described in Example 12 (ii) to give 4-cyano-2(2-furanyl) phenyl hydantoin as a tan coloured solid.

ii) 4-Cyano-2-(2-furanyl)phenyl hydantoin was hydrolysed using the method described in Example 1 (iii) to give the title product as a white solid, m.p. 189°–196° C. dec.

EXAMPLE 14

2-Amino-2-(2-methyl-3,5-dihydroxyphenyl)-acetic acid i) To 50% sodium hydride (previously washed with 40°–60° C. petroleum spirit) (10.56 g, 220 mmol), covered with dry dimethylformamide (DMF) (50 ml) under nitrogen pressure in a 1 L 3-necked round-bottomed flask cooled in a ice-bath, was added a solution of methyl 3,5-dihydroxybenzoate (16.80 g, 100 mmol) in dry DMF (200 ml). The reaction mixture was then allowed to warm to ambient temperature and stirred for 45 minutes, and a solution of benzyl bromide (37.62 g, 220 mmol) in dry DMF (50 ml) was added dropwise. The reaction mixture was then stirred at ambient temperature for a further 2 hours.

The reaction mixture was then poured into a stirred, saturated solution of ammonium chloride (600 ml), and extracted with diethyl ether (3×). The combined ether extracts were washed in turn with (1) 1M sodium hydroxide, (2) $H_2O$, (3) saturated sodium chloride, dried over magnesium sulphate, filtered and evaporated in vacuo to give methyl 3,5-dibenzyloxybenzoate as a light-yellow oil.

ii) Methyl 3,5-dibenzyloxybenzoate (18.00 g, 52 mmol), and lithium hydroxide (7.0 g, 156 mmol) were dissolved in a mixture of tetrahydrofuran/water (7:1) (200 ml) and the mixture stirred at ambient temperature for 24 hours.

After this time the reaction was diluted with more water (400 ml), washed with hexane, and then acidified with 2M hydrochloric acid to pH2. The acidified aqueous phase was then extracted with ethyl acetate (3×) and the combined organic extracts washed with (1) $H_2O$, (2) saturated brine, dried over magnesium sulphate, filtered and evaporated in vacuo to give 3,5-dibenzyloxybenzoic acid as a white solid.

iii) To a suspension of 3,5-dibenzyloxybenzoic acid (14.7 g, 44 mmol) in dry benzene (35 ml) was added, dropwise, thionyl chloride (9.65 ml, 132 mmol). The mixture was then heated under reflux, to give a clear, dark solution. After 1.5 hours the reaction mixture was allowed to cool, and then evaporated in vacuo to give an amber oil, which crystallised on standing.

The crude acid chloride was then dissolved in dry $CH_2Cl_2$ (25 ml) and the solution added dropwise to a solution of 2-amino-2-methyl-1-propanol (7.84 g, 88 mmol) in $CH_2Cl_2$ (25 ml) at 5° C. (ice-bath). The mixture was then stirred at ambient temperature for 2 hours before filtering over celite. The filtrates were washed with water, dried over magnesium sulphate, filtered and evaporated in vacuo to give a dark oil.

To the stirred, crude amide was then added, dropwise, thionyl chloride (9.65 ml, 132 mmol). When addition was complete, the liquid was poured into stirred, dry diethyl ether (150 ml). The ether was then decanted off, the oil dissolved in ethanol (150 ml) and the solution poured into stirred, ice-cold 5M sodium hydroxide (40 ml). The basic solution was then extracted with diethyl ether (3×), and the combined ethereal extracts dried over magnesium sulphate, filtered and evaporated to give a dark oil. The crude oil was purified by flash chromatography on silica (eluant hexane:diethyl ether=1:1) to give 4,4-dimethyl-2-(3,5-dibenzyloxyphenyl)-oxazoline as a yellow solid.

iv) To a stirred solution of 4,4-dimethyl-2-(3,5-dibenzyloxyphenyl)-oxazoline (5.00 g, 13.3 mmol) in dry dimethoxyethane (DME) (50 ml), under positive nitrogen pressure and cooled to −78° C. in an acetone/dry ice-bath, was added, dropwise, n-butyl-lithium (9.2 ml of 1.6M hexane solution, 14.6 mmol). (Rapid development of dark green colouration.) After stirring at −78° C. for 1.5 hours, iodomethane (4.2 ml, 66.6 mmol) was added dropwise. (Colour change to dark orange.) After one hour at −78° C. the reaction mixture was allowed to warm to ambient temperature and stirred for a further two hours.

The reaction mixture was quenched cautiously with water (100 ml) and extracted with diethyl ether (3×). The combined ethereal extracts were washed with saturated sodium bicarbonate solution, dried over magnesium sulphate, filtered and evaporated in vacuo to give a viscous amber oil (5.32 g). The crude product was purified by flash chromatography on silica (eluant hexane:diethyl ether=2:1) to give 4,4-dimethyl-2-(2-methyl-3,5-dibenzyloxyphenyl)-oxazoline as a white solid.

v) A solution of 4,4-dimethyl-2-(2-methyl-3,5-dibenzyloxyphenyl)-oxazoline (2.55 g, 6.55 mmol) in iodomethane (9 ml) was heated to reflux, under positive nitrogen pressure, for 16 hours. The solution was then evaporated in vacuo to give the quatenary salt as a yellow foam.

To a solution of the quatenary salt in methanol (50 ml), cooled in an ice bath, was added sodium borohydride (200 mg, 5.3 mmol) (in 4×50 mg portions over 2 hours). The reaction mixture was then stirred at ambient temperature. After 2 hours, 2M hydrochloric acid (20 ml) was added and the reaction mixture stirred for 16 hours.

The reaction mixture was then diluted with water (100 ml) and extracted with ethyl acetate (3×). The combined organic extracts were washed with (1) 10% sodium dithionite, (2) saturated brine, dried over magnesium sulphate, filtered and evaporated in vacuo to give a yellow solid. The crude product was purified by flash chromatography on silica (eluant hexane:diethyl ether=1:1) to give 2-methyl-3,5-dibenzyloxybenzaldehyde.

vi) A mixture of 2-methyl-3,5-dibenzyloxybenzaldehyde (1.1 g, 3.3 mmol), potassium cyanide (860 mg, 13.3 mmol), ammonium carbonate (1.27 g, 13.3 mmol) and ammonium chloride (177 mg, 3.3 mmol) in a mixture of ethanol/water (2:1) (35 ml) was heated in a sealed vessel at 80° C. for 20 hours.

The reaction was allowed to cool and then acidified to pH2 with concentrated hydrochloric acid. The precipitated light yellow solid was collected by filtration, washed with water and dried in vacuo at 50° C. to yield 5-(2-methyl-3,5-dibenzyloxyphenyl)-hydantoin as a light yellow solid.

vii) A solution of 5-(2-methyl-3,5-dibenzyloxyphenyl)-hydantoin (1.13 g, 2.8 mmol) in methanol (100 ml) was shaken in a Parr hydrogenation apparatus at 60 p.s.i. over 10% Palladium/charcoal (120 mg) for 6 hours. The reaction suspension was filtered over celite and the filtrate evaporated in vacuo to give 5-(2-methyl-3,5-dihydroxyphenyl)-hydantoin as an off-white solid.

viii) A solution of 5-(2-methyl-3,5-dihydroxyphenyl)-hydantoin (400 mg, 1.8 mmol) in 2M sodium hydroxide (4.5 ml, 9 mmol) was heated in a sealed vessel at 110° C. for 48 hours. The reaction mixture was allowed to cool, neutralised with 2M hydrochloric acid and purified by cation-exchange chromatography (Dowex 50×8–100; column eluted sequentially with water,water:THF 1:1 and water again. The amino acid was finally eluted with water:pyridine 9:1). The pyridine was removed in vacuo and the residual solid redissolved in water and freeze-dried to give the title compound as a light brown solid, m.p. 215° C. (dec).

EXAMPLE 15

2-(4-Carboxy-2-ethylphenyl)glycine i) A mixture of 4-cyano-2-trifluoromethylsulphonyl-benzaldehyde (0.91 g, 3.26 mmol), tris (dibenzylidenacetone)dipalladium(0) (67 mg, 0.074 mmol), tris(2-furyl)phosphine (34 mg, 0.15 mmol) and anhydrous lithium chloride (0.47 g, 11.04 mmol) in dry N-methylpyrrolidinone (10 ml) was stirred under an atmosphere of nitrogen at room temperature for 5 minutes. Vinyltri-n-butyltin (1.31 g, 4.08 mmol) was added and the solution stirred at room temperature fo 22 hours. A saturated solution of potassium fluoride (15 ml) was then added, followed by diethyl ether (15 ml). After stirring for 5 minutes, the resulting yellow suspension was filtered through celite and the solids washed with diethyl ether. The filtrate layers were separated and the organic phase washed once with a saturated solution of potassium fluoride, dried, filtered and evaporated to give 4-cyano-2-vinylbenzaldehyde as a pale yellow solid.

ii) A stirred mixture of 4-cyano-2-vinylbenzaldehyde (0.24 g, 1.53 mmol), potassium cyanide (0.2 g, 3.06 mmol) and ammonium carbonate (0.59 g, 6.12 mmol) in ethanol-water (1:1, 6 ml) was heated to 85° C. for 17 hours following the procedure described in Example 1 part (ii). The crude solid obtained after extraction was chromatographed on flash silica eluting with ethyl acetate-hexane (4:1) to give 5-(4-cyano-2-vinylphenyl)hydantoin as a gum.

iii) A solution of 5-(4-cyano-2-vinylphenyl)hydantoin (75 mg, 0.35 mmol) in methanol (20 ml) was shaken with 10% palladium-carbon (10 mg) under an atmosphere of hydrogen for 0.5 hours at 25 p.s.i. The catalyst was removed by filtration to give 5-(4-cyano-2-ethylphenyl) hydantoin in a quantitative yield as a colourless oil.

iv) 5-(4-Cyano-2-ethylphenyl)hydantoin (75 mg, 0.35 mmol) was hydrolysed with aqueous sodium hydroxide (2M, 1 ml) at 120° C. for 120 hours and worked up following the procedure described in Example 1 (iii) to give the title compound as a white solid, m.p. 189°–193° C.

EXAMPLE 16

2-[4-Carboxy-2-(2-phenylethyl)phenyl]glycine i) A mixture of 4-cyano-2-trifluoromethylsulphonyl-benzaldehyde (1.75 g, 6.3 mmol), tris (dibenzylidenacetone)dipalladium(o) (116 mg, 0.13 mmol), tris(2-furyl)phosphine (234 mg, 1.0 mmol) and anhydrous lithium chloride (0.8 g, 18.9 mmol) in dry N-methyl pyrrolidinone (18 ml) were reacted with (phenylethynyl)tri-n-butyltin (2.91 g, 7.4 mmol) for 3 hours at 50° C. and worked up following the procedure described in Example 15 (i). The crude oil was chromatographed on flash silica eluting with hexane-diethyl ether (4:1) to give 4-cyano-2-(2-phenylethynyl)benzaldehyde as a yellow solid.

ii) A stirred mixture of 4-cyano-2-(2-phenylethynyl) benzaldehyde (0.69 g, 3.0 mmol), potassium cyanide (0.39 g, 6.0 mmol) and ammonium carbonate (1.15 g, 12 mmol) in ethanol-water (1:1, 12 ml) was heated to 85° C. for 4 hours following the procedure described in Example 1 (ii). The crude solid obtained after extraction was chromatographed on flash silica eluting with ether to give 5-[4-cyano-2-(2-phenylethynyl)phenyl]hydantoin as a yellow foam.

iii) A solution of 5-[4-cyano-2-(2-phenylethynyl)phenyl] hydantoin (100 mg, 0.33 mmol) in methanol (20 ml) was shaken with 10% palladium-carbon (10 mg) under an atmosphere of hydrogen for 24 hours at 60 p.s.i. The catalyst was removed by filtration to give 5-[4-cyano-2-(2-phenylethyl)phenyl]hydantoin as a colourless oil.

iv) 5-[4-Cyano-2-(2-phenylethyl)phenyl]hydantoin (53 mg, 0.17 mmol) was hydrolysed with aqueous sodium hydroxide (2M, 0.52 ml) at 120° C. for 18 hours and worked up following the procedure described in Example 1 (iii) to give the title compound as a white solid.

EXAMPLE 17

2-[4-Carboxy-2-(2-isopropenyl)phenyl]glycine i) A solution of 4-cyano-2-trifluoromethylsulphonyl-benzaldehyde (2.35 g, 8.44 mmol), tris (dibenzylidenacetone)dipalladium(o) (0.24 g, 0.26 mmol) and triphenylarsine (0.64 g, 2.08 mmol) in dry N-methylpyrrolidinone (25 ml) was stirred at room temperature under an atmosphere of nitrogen until the purple colour had discharged (ca. 2 minutes). A solution of 2-tri-n-butylstannylpropene (3.1 g, 9.37 mmol) in dry N-methylpyrroldinone (20 ml) was added dropwise and the mixture heated at 80° C. overnight. The cooled mixture was treated with a saturated solution of potassium fluoride (15 ml) and ethyl acetate (25 ml) and stirred at room temperature for 30 minutes. The suspension was filtered through celite and the solids washed with ethyl acetate. The organic phase was separated and washed with water (3×) and a saturated solution of ammonium chloride, dried, filtered and evaporated to an oil. Chromatography on flash silica eluting with hexane-dichloromethane (7:3, 1:1) gave 4-cyano-2-(2-isopropenyl)benzaldehyde as a colourless oil which solidified on standing.

ii) A stirred mixture of 4-cyano-2-(2-isopropenyl) benzaldehyde (1.0 g, 5.85 mmol), potassium cyanide (0.68 g, 10.53 mmol) and ammonium carbonate (2.0 g, 21 mmol) in ethanol-water (1;1, 12 ml) was heated to 80° C. for 3 hours following the procedure described in Example 1 (ii). The crude oil obtained after extraction was chromatographed on flash silica eluting with dichloromethane then dichloromethane-ethyl acetate (4:1, 3:2) to give 5-[4-cyano-2-(2-isopropenyl)phenyl]hydantoin as a pale yellow foam, m.p. (from chloroform) 196°–199° C.

iii) A solution of 5-[4-cyano-2-(2-isopropenyl) phenyl] hydantoin (50 mg, 0.21 mmol), di-t-butyldicarbonate (113 mg, 0.52 mmol) and 4-dimethylaminopyridine (catalytic amount) in dichloromethane (10 ml) was stirred at room temperature under an atmosphere of nitrogen overnight. The mixture was filtered through a pad of flash silica under suction eluting with diethyl ether (100 ml) to give a quantitative yield of N1,N3-bis(t-butyloxycarbonyl)-5-[4-cyano-2-(2-isopropenyl) phenyl]hydantoin as a colourless glass.

iv) N1,N3-Bis(t-butyloxycarbonyl)-5-[4-cyano-2-(2-isopropenyl)phenyl]hydantoin (90 mg, 0.2 mmol) was stirred with aqueous lithium hydroxide (1M, 2 ml) in tetrahydrofuran (4 ml) for one week at room temperature. The mixture was acidified with acetic acid (0.13 ml) and chromatographed on ion exchange resin by the procedure described in Example 1 (iii) to give the title compound as a white solid, m.p. >250° C.

EXAMPLE 18

2-[4-Carboxy-2-(2-isopropyl)phenyl]glycine i) A solution of 5-[4-cyano-2-(2-isopropenyl) phenyl] hydantoin (0.5 g, 2.07 mmol) in methanol (25 ml) was shaken with 10% palladium-carbon (50 mg) under an atmosphere of hydrogen for 3 hours at 60 p.s.i. The catalyst was removed by filtration and the filtrate concentrated until crystallisation commenced. 5-[4-cyano-2-(2-isopropyl)phenyl]hydantoin was collected as a white solid.

ii) 5-[4-Cyano-2-(2-isopropyl)phenyl]hydantoin (0.15 g, 0.62 mmol) was hydrolysed with aqueous sodium hydroxide (2M, 1.85 ml) at 120° C. for 2 days and worked up by the procedure described in Example 1 (iii) to give the title compound as a white solid, m.p. 197°–198° C.

EXAMPLE 19

2-(2-Butyl-4-carboxyphenyl)glycine i) A solution of 4-cyano-2-trifluoromethylsulphonyl-benzaldehyde (1.8 g, 6.45 mmol), tris(dibenzylidenacetone)dipalladium(o) (0.18 g, 0.2 mmol) and triphenylarsine (0.49 g, 1.6 mmol) in dry N-methylpyrrolidinone (20 ml) was reacted with neat tetra-n-butyltin at a temperature of 100° C. for 18 hours and worked up following the procedure described in Example 17 (i). The crude oil was chromatographed on flash silica eluting with hexane-dichloromethane (7:3, 1:1) to give 2-butyl-4-cyanobenzaldehyde as a colourless oil.

ii) A stirred mixture of 2-butyl-4-cyanobenzaldehyde (0.9 g, 4.8 mmol), potassium cyanide (0.63 g, 9.6 mmol) and ammonium carbonate (1.85 g, 19.2 mmol) in ethanol/water (1:1, 10 ml) was heated with stirring in a sealed vessel at 85° C. overnight. The resulting crude solution was cooled and acidified with 2N hydrochloric acid (10 ml), then extracted with ethyl acetate (3×20 ml), combined, dried, then evaporated to yield a brown oil. Flash chromatography eluting with ethyl acetate/hexane (4:1) gave a pale brown oil lining the flask. It was triturated with ether (20 ml) and filtered off to give 5-(2-butyl-4-cyanophenyl)hydantoin as a white solid.

iii) A stirred solution of 5-(2-butyl-4-cyanophenyl)hydantoin (0.25 g, 0.97 mmol) in 2M sodium hydroxide (3 ml, 5.84 mmol) was heated at 120° C. in a sealed vessel over the weekend. It was worked up as Example 4 (iii) to give the title compound as a white solid, m.p. 227° C.

EXAMPLE 20

2-Amino-2-(2-methyl-3-hydroxyphenyl)-acetic acid i) A solution of 3-hydroxybenzaldehyde (20.40 g, 200 mmol), propane-1,3-diol (12.74 g, 200 mmol) and p-toluene-sulphonic acid (200 mg) in dry benzene (200 ml) was heated under reflux under a Dean and Stark apparatus for 2 hours. The reaction mixture was allowed to cool and then washed with saturated sodium bicarbonate solution. 2-(3-hydroxyphenyl)-1,3-dioxane was crystallised from the cool benzene solution, and was collected by filtration as an off-white solid, m.p. 110°–111° C.

ii) To 50% sodium hydride (previously washed with 40°–60° C. petroleum spirit) (4.64 g, 96.5 mmol), covered with dry DMF (50 ml) under positive nitrogen pressure in a 1 L 3-necked round-bottomed flask cooled in an ice-bath, was added, dropwise, a solution of 2-(3-hydroxyphenyl)-1,3-dioxane (15.80 g, 87.7 mmol) in dry DMF (200 ml). The reaction mixture was allowed to warm to ambient temperature and then stirred for 45 minutes. The reaction was then recooled to ca. 5° C. in an ice-bath and a solution of chloromethylmethyl ether (8.83 g, 109.7 mmol) in dry DMF (50 ml) added dropwise. The reaction mixture was again allowed to warm to ambient and then stirring continued for a further 2 hours.

The reaction mixture was poured into a stirred, saturated solution of ammonium chloride (600 ml), and extracted with diethyl ether (3×). The combined ethereal extracts were washed with (1) 1M NaoH, (2) water, (3) saturated brine, dried over magnesium sulphate, filtered and evaporated in vacuo to give 2-[3-(methoxymethyleneoxy)phenyl]-1,3-dioxane as a yellow, mobile oil.

iii) To a solution of 2-(3-[methoxymethyleneoxy]phenyl)-1,3-dioxane (11.0 g, 49.1 mmol) in cyclohexane (250 ml), under positive nitrogen pressure, and immersed in an ultrasonic bath filled with ice-water, was added sec-butyllithium (83.5 ml of 1.3M cyclohexane solution, 108 mmol). An orange-brown suspension was produced. The mixture was left in the ultrasonic bath at ca. 5° C. for 1 hour, then iodomethane (15.3 ml, 245.5 mmol) added dropwise. The ultrasonic bath was then charged with water at ambient temperature and the reaction mixture immersed in it for 16 hours.

The reaction mixture was poured into water (300 ml) and extracted with diethyl ether (3×). The combined ethereal extracts were washed with (1) water, (2) saturated brine, dried over magnesium sulphate, filtered and evaporated in vacuo to give a yellow oil. The crude product was purified by flash chromatography on silica (eluant hexane:diethyl ether=3:1) to give 2-[2-methyl-3-(methoxymethyleneoxy) phenyl]-1,3-dioxane as a clear oil.

iv) A solution of 2-[2-methyl-3-(methoxymethyleneoxy)-phenyl]-1,3-dioxane (0.65 g, 2.73 mmol) in a mixture of THF:5M HCl (1:1) (50 ml) was stirred at ambient temperature for 20 hours.

The reaction mixture was diluted with water (50 ml) and extracted with ethyl acetate (3×). The combined organic extracts were washed wih (1) water, (2) saturated brine, dried over magnesium sulphate, filtered and evaporated in vacuo to give 2-methyl-3-hydroxybenzaldehyde as a white solid.

v) A mixture of 2-methyl-3-hydroxybenzaldehyde (425 mg, 3.12 mmol), potassium cyanide (406 mg, 6.24 mmol), ammonium carbonate (600 mg, 6.24 mmol) and ammonium chloride (167 mg, 3.12 mmol) in a mixture of ethanol/water (1:1) (20 ml) was heated at 80° C. in a sealed vessel for 20 hours.

The reaction mixture was allowed to cool to ambient temperature, diluted with water (10 ml), acidified with concentrated hydrochloric acid and extracted with ethyl acetate (3×). The combined organic extracts were washed with saturated brine, dried over magnesium sulphate, filtered and evaporated in vacuo to give 5-(2-methyl-3-hydroxyphenyl)-1(H)-hydantoin as an off-white foam.

vi) A solution of 5-(2-methyl-3-hydroxyphenyl)-1(H)-hydantoin (230 mg, 1.11 mmol) in 2M sodium hydroxide (2.8 ml, 5.55 mmol) was heated at 110° C. in a sealed vessel for 60 hours.

The reaction mixture was allowed to cool, neutralised with 2M hydrochloric acid, and purified by cationic exchange chromatography (as in Example 14) to give the title compound as a fluffy white solid, m.p. 210° C. (dec).

EXAMPLE 21

2-Amino-2-(2-propyl-3,5-dihydroxyphenyl)-acetic acid i) 4-4-Dimethyl-2-(2-allyl-3,5-dibenzyloxyphenyl) oxazoline prepared by the method of Example 14 (i)–(iv).

ii) 2-Allyl-3,5-dibenzyloxybenzaldehyde prepared by the method of Example 14 (v).

iii) 5-(2-Allyl-3,5-dibenzyloxyphenyl)-1(H)-hydantoin prepared by the method of Example 14 (vi).

iv) 5-(2-Propyl-3,5-dihydroxyphenyl)-1(H)-hydantoin prepared by the method of Example 14 (vii).
v) 2-Amino-2-(2-propyl-3,5-dihydroxyphenyl)-acetic acid prepared by the method of Example 14 (viii), to give a light brown hygroscopic solid.

EXAMPLE 22

2-Amino-2-(2-benzyl-3,5-dihydroxyhenyl)-acetic acid i) 4,4-Dimethyl-2-(2-benzyl-3,5-dibenzyloxyphenyl) oxazoline prepared by the method of Example 14 (i)–(iv).
ii) 2-Benzyl-3,5-dibenzyloxybenzaldehyde prepared by the method of Example 14 (v).
iii) 5-(2-Benzyl-3,5-dibenzyloxyphenyl)-1(H)-hydantoin prepared by the method of Example 14 (vi).
iv) 5-(2-Benzyl-3,5-dihydroxyphenyl)-1(H)-hydantoin prepared by the method of Example 14 (vii).
v) 2-Amino-2-(2-benzyl-3,5-dihydroxyphenyl)-acetic acid prepared by the method of Example 14 (viii), to give a fluffy white solid, m.p. 198°–200° C.

EXAMPLE 23

2-Amino-2-(2-nitro-3,5-dihydroxyphenyl)-acetic acid

2-Amino-2-(3,5-dihydroxyphenyl)-acetic acid (183 mg, 1 mmol) was added portionwise to stirred 5.5M nitric acid (2.5 ml, 15 mmol), which has been cooled to −10° C. in an ice/salt bath. The resulting brown solution was diluted with water (2 ml), neutralised with 2M sodium hydroxide, and purified by cationic exchange chromatography (as in Example 14) to give the title compound as a fluffy yellow solid, m.p. >280° C.

EXAMPLE 24

2-Amino-2-(2-methyl-3-hydroxy-4-carboxyphenyl)-acetic acid i) A mixture of 2-methyl-3-hydroxybenzaldehyde (synthesised by the methods of Example 20 (i)–(iv)) (2.35 g, 17.3 mmol) and dimethylcarbamoyl chloride (2.7 ml, 21.5 mmol) in dry pyridine (30 ml) was stirred at 90° C. for 16 hours.

The reaction mixture was cooled, poured into water (200 ml) and extracted with ethyl acetate (3×). The combined organic extracts were washed with (1) water, (2) saturated brine, dried over magnesium sulphate, filtered and evaporated in vacuo to give an amber oil (3.60 g, 89%). The crude oil was purified by flash chromatography on silica (eluant hexane:diethyl ether=1:1) to give 2-methyl-3-(diethylaminocarbonyloxy)benzaldehyde as a mobile yellow oil.

ii) To a solution of N-methyl piperazine (1.26 g, 12.6 mmol) in dry tetrahydrofuron (THF) (120 ml) under positive nitrogen pressure at 0°–5° C. was added n-butyl lithium (7.9 ml of 1.6M hexane solution, 12.6 mmol). After stirring at 0°–5° C. for 20 minutes, a solution of 2-methyl-3-(diethylaminocarbonyloxy)-benzaldehyde (2.45 g, 10.5 mmol) in dry THF (30 ml) was added, followed by tetramethylethylenediamine (3.2 ml, 21 mmol). After stirring at 0°–5° C. for a further 10 minutes, the reaction was cooled to −78° C. (dry ice/acetone bath) and t-butyllithium (7.4 ml, of 1.7 molar pentane solution, 12.6 mmol) was added, to give a dark orange solution. After stirring at −78° C. for 1 hour, the solution was saturated with gaseous carbon dioxide, allowed to warm to ambient temperature, and stirred for a further 90 minutes.

After this time the reaction mixture was poured into stirred 2M hydrochloric acid and extracted with ethyl acetate (3×) The combined organic extracts were dried over magnesium sulphate, filtered and evaporated in vacuo to give a yellow gum. The gum was dissolved in diethyl ether, and extracted into saturated sodium bicarbonate solution (3×). The combined basic extracts were backwashed with diethyl ether, acidified with concentrated hydrochloric acid, and extracted with ethyl acetate (3×). The combined organic extracts were dried over magnesium sulphate, filtered, and evaporated in vacuo to give a yellow foam. This solid was finally purified by flash chromatography on silica (eluant:diethyl ether 0.1% glacial acetic acid) to give 2-(diethylaminocarbonyloxy)-3-methyl-4-formylbenzoic acid as a white crystalline solid.

iii) A solution of 2-(diethylaminocarbonyloxy)-2-methyl-4-formylbenzoic acid (100 mg, 0.36 mmol) in methanol saturated with hydrogen chloride (10 ml) was stirred at ambient temperature for 24 hours.

The reaction mixture was poured into water (50 ml) and extracted with diethyl ether (3×). The combined ethereal extracts were washed with (1) water, (2) saturated brine, dried over magnesium sulphate, filtered and evaporated in vacuo to give methyl-2-(diethylaminocarbonyloxy)-3-methyl-4-formylbenzoate as a clear, mobile oil.

iv) A mixture of basic alumina (1.33 g), potassium cyanide (133 mg, 2 mmol), ammonium chloride (120 mg, 2 mmol) and acetonitrile (20 ml) was immersed in an ultrasonic bath at 40° C. for 1 hour. A solution of methyl-2-(diethylaminocarbonyloxy)-3-methyl-4-formylbenzoate (120 mg, 0.41 mmol) in acetonitrile (5 ml) was then added, and immersion in the ultrasonic bath at 40° C. continued for a further 16 hours. The reaction mixture was filtered over celite, and the filtrates evaporated in vacuo to give the aminonitrile as a yellow oil.

The aminonitrile and diisopropylethylamine (0.106 ml, 0.37 mmol) were dissolved in dry dichloromethane (2 ml) and acetyl chloride (0.44 ml, 0.37 mmol) added. The solution was stirred at ambient temperature for 2 hours. The reaction mixture was evaporated in vacuo, diethyl ether added and the suspension filtered. The filtrate was subjected to flash chromatography on silica (eluant diethyl ether) to give methyl-2-(diethylaminocarbonyloxy)-3-methyl-4-(2-acetylaminoacetonitrilo-2-yl)-benzoate as a white solid.

v) A mixture of methyl-2-(diethylaminocarbonyloxy)-3-methyl-4-(2-acetylaminoacetonitrilo-2-yl)-benzoate (34 mg, 0.094 mmol) and 5M hydrochloric acid (2 ml) were heated at 80° C. in a sealed vessel for 48 hours.

The reaction mixture was allowed to cool and then evaporated in vacuo to give the hydrochloride salt of the product. The salt was dissolved in water and purified by cationic exchange chromatography (as in Example 14) to give the title compound as a fluffy off-white solid, m.p. >260° C.

EXAMPLE 25

2-Amino-2-(2-[3-phenylpropyl]-3-hydroxy-4-carboxyphenyl)-acetic acid i) 2-(2-[3-cinnamyl]-3-[methoxymethyleneoxy]phenyl)-1,3-dioxane Prepared by the method of Example 20 (iii) using 2-[3-(methoxymethyleneoxy)phenyl]-1,3-dioxane (8.20 mg, 36.6 mmol), sec-butyllithium (62 ml, 80.5 mmol) and cinnamyl bromide (8.65 g, 43.9 mmol) in cyclohexane (250 ml) to give a yellow oil.

ii) 2-(2-[3-Phenylpropyl]-3-[methoxymethyleneoxy]phenyl)-1,3-dioxane

A solution of 2-(2-[3-cinnamyl]-3-[methoxymethyleneoxy]phenyl)-1,3-dioxane (3.40 g, 10 mmol) in ethyl acetate (100 ml) was shaken in a Parr hydrogenation apparatus at 60 p.s.i. over 10% Palladium/charcoal (100 mg) for 4 hours.

The reaction suspension was filtered over celite and the filtrate evaporated in vacuo to give the product as a yellow oil.

iii) 2-(3-Phenylpropyl)-3-hydroxybenzaldehyde

Prepared by the method of Example 20 (iv) to give a yellow solid, m.p. 118°–122° C.

iv) 2-(3-Phenylpropyl)-3-(diethylaminocarbonyloxy)-benzaldehyde

Prepared by the method of Example 24 (i) to give a yellow oil.

v) 2-(Diethylaminocarbonyloxy)-3-(3-phenylpropyl)-4-formylbenzoic acid

Prepared by the method of Example 24(ii) to give an off-white gum.

vi) Methyl-2-(diethylaminocarbonyloxy)-3-(3-phenylpropyl)-4-formylbenzoate

Prepared by the method of Example 24 (iii) to give a yellow oil.

vii) Methyl-2-(diethylaminocarbonyloxy)-3-(3-phenylpropyl)-4-(2-acetylamino-acetonitrilo-2-yl)benzoate Prepared by the method of Example 24 (iv) to give a white solid.

viii) 2-Amino-2-(2-[3-phenylpropyl]-3-hydroxy-4-carboxyphenyl) acetic acid

Prepared by the method of Example 24 (v) to give the title compound as a white solid, m.p. >250° C.

EXAMPLE 26

2-(4-Carboxy-3-hydroxy-6-methylphenyl)glycine i) To a stirred solution of 2-methoxy-5-methylphenyl (2.5 g, 18.09 mmol) in trifluoroacetic acid (40 ml) at room temperature was added solid α-methoxyhippuric acid methyl ester (4 g, 17.92 mmol) portionwise. The resulting solution was stirred for 1.5 hours at room temperature, cooled in an ice-bath and diluted with water (70 ml). The mixture was extracted with ethyl acetate (2×) and the combined extracts washed with water and a saturated solution of sodium chloride, dried, filtered and evaporated to an oil. Crystallisation from diethyl ether-hexane gave methyl 2-benzamido-2-(4-hydroxy-3-methoxy-6-methylphenyl)acetate as a white solid.

ii) To a solution of methyl 2-benzamido-2-(4-hydroxy-3-methoxy-6-methylphenyl)acetate (0.5 g, 1.51 mmol), 2,6-lutidine (0.24 g, 2.24 mmol) and 4-dimethylaminopyridine (45 mg, 0.37 mmol) in dry dichloromethane (10 ml) stirred under an atmosphere of nitrogen and cooled to −50° C. was added trifluoromethanesulphonic anhydride (0.62 g, 2.20 mmol). The mixture was kept between −25° to −35° C. for 1.5 hours, diluted with water and extracted with dichloromethane. The extract was washed with aqueous hydrochloric acid (1M), water (2×) and a saturated solution of sodium chloride, dried, filtered and evaporated to a white solid. This was triturated with diethyl ether to give methyl 2-benzamido-2-(3-methoxy-6-methyl-4-trifluoromethylsulphonylphenyl)acetate.

iii) A stirred mixture of methyl 2-benzamido-2-(3-methoxy-6-methyl-4-trifluoromethylsulphonylphenyl)acetate (0.3 g, 0.65 mmol) triethylamine (0.16 g, 1.6 mmol), palladium acetate (5 mg, 0.022 mmol) and 1,3-diphenylphosphinopropane (9 mg, 0.022 mmol) in dimethylformamide (3 ml) and methanol was saturated with carbon monoxide gas using a bubbler and then heated to 70° C. for 3 hours and overnight at room temperature under an atmosphere of carbon monoxide using a gas filled balloon. The mixture was acidified with aqueous hydrochloric acid (2M) and extracted with ethyl acetate (2×). The combined extracts were washed with a saturated solution of ammonium chloride, dried, filtered and evaporated to a solid. Chromatography on flash silica eluting with diethyl ether-hexane (3:2, 4:1) gave methyl 2-benzamido-2-(4-methoxycarbonyl-3-methoxy-6-methylphenyl)acetate as a white solid.

iv) A stirred suspension of methyl 2-benzamido-2-(4-methoxycarbonyl-3-methoxy-6-methylphenyl)acetate (120 mg, 0.32 mmol) in aqueous hydrochloric acid (5M, 3 ml) was heated to 110° C. for 7 days in a PTFE lined stainless steel sealed reaction vessel. The contents were periodically cooled, evaporated and topped up with an equivalent amount of fresh aqueous hydrochloric acid. The contents were cooled and chromatographed on ion exchange resin following the procedure described in Example 1 (iii) to give the title compound as an off-white solid, m.p. >250° C.

The following formulations can be prepared using a compound of the invention as active ingredient.

EXAMPLE 27

Soft gelatin capsule

Each soft gelatin capsule contains:

| Active ingredient | 150 mg |
| Arachis oil | 150 mg |

After mixing together, the blend is filled into soft gelatin capsules using the appropriate equipment.

EXAMPLE 28

Hard gelatin capsule

Each active capsule contains:

| Active ingredient | 50 mg |
| PEG 4000 | 250 mg |

The PEG 4000 is melted and mixed with the active ingredient. Whilst still molten the mixture is filled into capsule shells and allowed to cool.

EXAMPLE 29

Tablets each containing 10 mg of active ingredient are made up as follows:

| Active ingredient | 10 mg |
| Starch | 160 mg |
| Microcrystalline cellulose | 100 mg |
| Polyvinylpyrrolidone (as 10% solution in water) | 13 mg |

-continued

| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

We claim:

1. A compound of the formula:

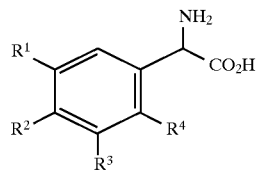

in which $R^1$ is hydrogen, hydroxy or $C_{1-6}$ alkoxy, $R^2$ is hydrogen, carboxy, tetrazolyl, —$SO_2H$, —$SO_3H$, —$OSO_3H$, —CONHOH, or —P(OH)OR', —PO(OH)OR', —OP(OH)OR' or —OPO(OH)OR' where R' is hydrogen, $C_{1-6}$ alkyl, $C_{2-6}$ alkenyl or aryl $C_{1-6}$ alkyl, $R^3$ is hydrogen, hydroxy or $C_{1-4}$ alkoxy, and $R^4$ is fluoro, trifluoromethyl, nitro, $C_{1-6}$ alkyl, $C_{3-7}$ cycloalkyl, $C_{2-6}$ alkenyl, $C_{2-6}$ alkynyl, $C_{1-6}$ alkylthio, heteroaryl, optionally substituted aryl, optionally substituted aryl $C_{1-6}$ alkyl, optionally substituted aryl $C_{2-6}$ alkenyl, optionally substituted aryl $C_{2-6}$ alkynyl, optionally substituted aryloxy, optionally substituted aryl $C_{1-6}$ alkoxy, optionally substituted arylthio, optionally substituted aryl $C_{1-6}$ alkylthio or —CONR"R'", —$SO_2NR"R'"$, —NR"R'", —OCONR"R'" or —SONR"R'" where R" and R'" are each hydrogen, $C_{1-6}$ alkyl or aryl $C_{1-6}$ alkyl, or R" and R'" together form a $C_{3-7}$, any optionally substituted aryl group being an aryl group that is unsubstituted or substituted by one to three substituents selected from the group consisting of $C_{1-4}$ alkyl, $C_{1-4}$ alkoxy, carboxy, hydroxy, cyano, halo, trifluoromethyl, nitro, amino, $C_{1-4}$ acylamino, and $C_{1-4}$ alkylthio;

provided that (i) $R^1$, $R^2$ and $R^3$ are not all hydrogen, and (ii) when $R^2$ and $R^3$ are hydrogen and $R^1$ is hydroxy, $R^4$ is not fluoro;

or a salt or ester thereof.

2. A compound according to claim 1 in which $R^1$ and $R^3$ are each hydrogen or hydroxy.

3. A compound according to claim 1 in which $R^1$ is hydrogen, $R^2$ is carboxy, $R^3$ is hydrogen or hydroxy and $R^4$ is $C_{1-6}$ alkyl.

4. A compound according to claim 1 in which $R^1$ is hydrogen or hydroxy, $R^2$ is hydrogen or carboxy, $R^3$ is hydrogen or hydroxyl and $R^4$ is $C_{1-6}$ alkyl, $C_{2-6}$ alkenyl, optionally substituted phenyl, optionally substituted phenyl $C_{1-6}$ alkyl, optionally substituted phenoxy, optionally substituted phenylthio or optionally substituted phenyl $C_{1-6}$ alkylthio.

5. A compound according to claim 1 in which $R^1$ is hydrogen, $R^2$ is carboxy, $R^3$ is hydrogen.

6. A compound according to claim 1 in which $R^1$ is hydroxyl, $R^2$ is hydrogen, $R^3$ is hydroxyl and $R^4$ is $C_{1-6}$ alkyl or optionally substituted phenyl $C_{1-6}$ alkyl.

7. A compound according to claim 1 in which $R^1$ is hydrogen, $R^2$ is carboxy, $R^3$ is hydroxyl and $R^4$ is $C_{1-6}$ alkyl or optionally substituted phenyl $C_{1-6}$ alkyl.

8. A compound as claimed in claim 1, which is selected from 2-(4-carboxy-2-methylphenyl)glycine, (S)-2-(4-carboxy-methylphenyl)glycine and 2-amino-2-(2-methyl-3-hydroxy-phenyl)acetic acid.

9. A pharmaceutical formulation comprising a compound according to any of claims 1–7 or a pharmaceutically-acceptable salt or ester thereof, together with a pharmaceutically-acceptable diluent or carrier therefor.

10. A method of treating an animal suffering from or susceptible to a disorder of the central nervous system, which comprises administering a compound according to claim 1 or a pharmaceutically acceptable salt or ester thereof.

11. A method as claimed in claim 10, in which said animal is a human.

12. A method of blocking metabotropic glutamate receptor second messenger responses in an animal, which comprises administering a compound as claimed in claim 1.

* * * * *